(12) United States Patent
Nygren et al.

(10) Patent No.: US 8,229,570 B2
(45) Date of Patent: Jul. 24, 2012

(54) IMPLANTABLE ELECTRODES HAVING ZIRCONIUM NITRIDE COATINGS

(75) Inventors: Lea A. Nygren, Bloomington, MN (US); Shawn D. Knowles, Saint Francis, MN (US)

(73) Assignee: Medtronic, Inc., Minneapolis, MN (US)

( * ) Notice: Subject to any disclaimer, the term of this patent is extended or adjusted under 35 U.S.C. 154(b) by 681 days.

(21) Appl. No.: 11/343,059

(22) Filed: Jan. 30, 2006

(65) Prior Publication Data

US 2007/0179374 A1    Aug. 2, 2007

(51) Int. Cl.
*A61N 1/00* (2006.01)
*A61B 5/04* (2006.01)

(52) U.S. Cl. ........................................ 607/116; 600/395
(58) Field of Classification Search ................ 607/116; 600/395
See application file for complete search history.

(56) References Cited

U.S. PATENT DOCUMENTS

| | | | |
|---|---|---|---|
| 4,405,427 A * | 9/1983 | Byrd ............................... 205/50 |
| 4,603,704 A * | 8/1986 | Mund et al. ................... 607/116 |
| 4,611,604 A * | 9/1986 | Botvidsson et al. .......... 607/122 |
| 4,895,765 A | 1/1990 | Sue et al. |
| 5,024,227 A * | 6/1991 | Schmid ......................... 600/391 |
| 5,181,526 A | 1/1993 | Yamasaki |
| 5,227,129 A | 7/1993 | Bryan et al. |
| 5,258,022 A | 11/1993 | Davidson |
| 5,496,359 A | 3/1996 | Davidson |
| 5,534,022 A | 7/1996 | Hoffmann et al. |
| 5,628,790 A | 5/1997 | Davidson |
| 5,647,858 A | 7/1997 | Davidson |
| 5,683,443 A | 11/1997 | Munshi et al. |
| 5,705,070 A | 1/1998 | Saaski et al. |
| 5,827,184 A * | 10/1998 | Netherly et al. .............. 600/372 |
| 6,135,953 A * | 10/2000 | Carim ........................... 600/372 |
| 6,224,985 B1 | 5/2001 | Shah et al. |
| 6,475,214 B1 * | 11/2002 | Moaddeb ........................ 606/41 |
| 6,650,922 B2 * | 11/2003 | Kurata et al. ................. 600/395 |
| 6,797,335 B1 * | 9/2004 | Paderov et al. ............... 427/530 |
| 7,042,093 B2 * | 5/2006 | Shimizu et al. .............. 257/758 |
| 2002/0091421 A1 * | 7/2002 | Greenberg et al. ............ 607/54 |
| 2002/0193845 A1 * | 12/2002 | Greenberg et al. ............ 607/54 |
| 2004/0004287 A1 * | 1/2004 | Shimizu et al. .............. 257/758 |
| 2004/0127966 A1 | 7/2004 | Fricks et al. |
| 2004/0240152 A1 | 12/2004 | Schott et al. |
| 2005/0049665 A1 | 3/2005 | Brabed et al. |
| 2005/0075709 A1 | 4/2005 | Brennan et al. |
| 2005/0246002 A1 * | 11/2005 | Martinez ....................... 607/116 |
| 2006/0052683 A1 * | 3/2006 | Parker et al. .................. 600/372 |
| 2006/0183989 A1 * | 8/2006 | Healy ............................ 600/372 |
| 2007/0089994 A1 * | 4/2007 | Zhou ............................. 205/264 |
| 2007/0092750 A1 * | 4/2007 | Zhou ............................. 428/670 |

(Continued)

FOREIGN PATENT DOCUMENTS

EP    1454651    9/2004

OTHER PUBLICATIONS

Masterton et al., "Chemical Principles with Qualitative Analysis," 6th Ed., Saunders College Publishing, Philadelphia, PA, 1986, pp. 237-239 and G-13.

(Continued)

*Primary Examiner* — Nicole F Lavert

(57) ABSTRACT

An implantable medical electrode comprising an electrode substrate having an exterior surface, and a zirconium nitride coating disposed over the exterior surface.

14 Claims, 3 Drawing Sheets

U.S. PATENT DOCUMENTS

| | | | |
|---|---|---|---|
| 2007/0092786 A1* | 4/2007 | Zhou | 429/44 |
| 2007/0123766 A1* | 5/2007 | Whalen et al. | 600/395 |
| 2007/0236867 A1* | 10/2007 | Hossick-Schott et al. | 361/523 |
| 2007/0293751 A1* | 12/2007 | Axelgaard et al. | 600/391 |
| 2008/0015669 A1* | 1/2008 | Jolly | 607/116 |
| 2008/0027525 A1* | 1/2008 | Frericks et al. | 607/118 |
| 2008/0077195 A1* | 3/2008 | Greenberg et al. | 607/54 |

OTHER PUBLICATIONS

*Hawley's Condensed Chemical Dictionary*: Thirteenth Edition, Revised by Richard J. Lewis, Sr., definition of "metal", p. 717, 1997.

Mattox, "Physical Vapor Deposition Processes," Society of Vacuum Coaters, Jan. 1992; pp. 44-45.

Nose, M., "Colorimetric Properties of ZrN and TiN Coatings", Surface and Coatings Technology, 142-144 (2001), pp. 211-217.

Hubler, R., "Wear and Corrosion Protection of 316-L Femoral Implants", Surface and Coatings Technology, 142-144 (2001), pp. 1078-1083.

Ramos H.J. et al., "Thin-film deposition of ZrN using a plasma-sputter type negative ion source". Vacuum, vol. 73, Apr. 19, 2004, pp. 549-554, XP002427914.

* cited by examiner

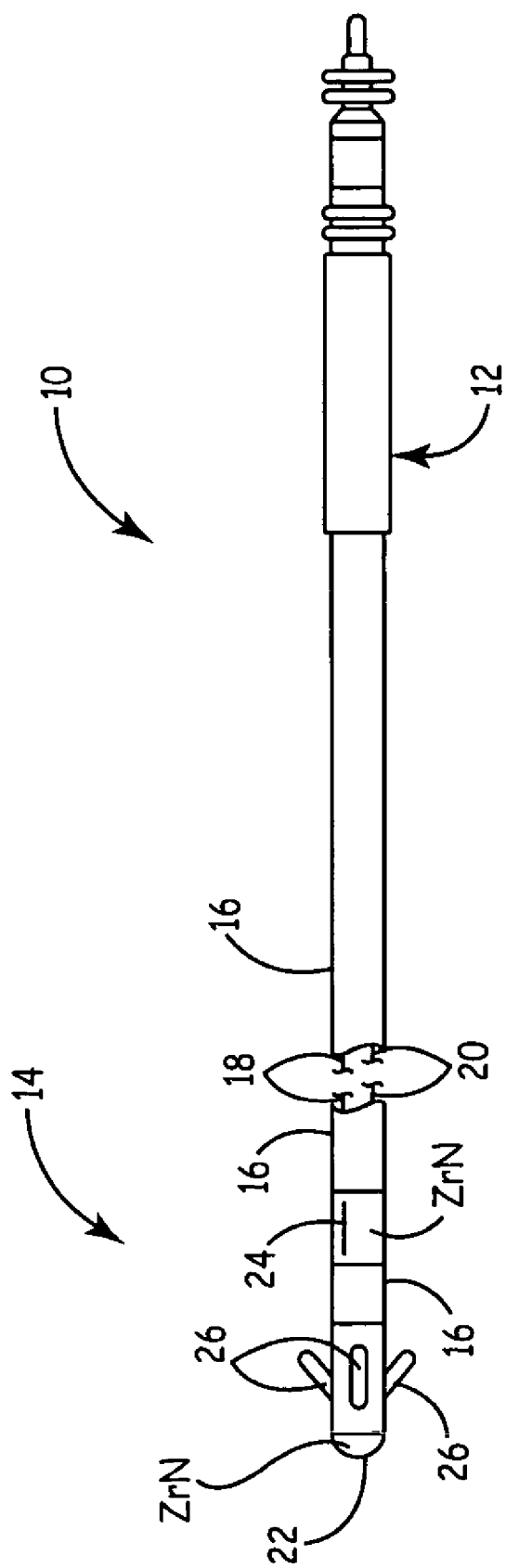

IMPLANTABLE ELECTRODES HAVING ZIRCONIUM NITRIDE COATINGS

BACKGROUND OF THE INVENTION

The present invention generally relates to implantable electrodes, and more particularly to implantable sensing and stimulating electrodes having reduced post-stimulation polarization.

Following delivery of stimulation (e.g., a cardiac pacing pulse), an electrode surface typically retains an accumulation of charge that persists for a period of time thereafter. This post-stimulation polarization may interfere with subsequent sensing of signals, such as intrinsic cardiac activity signals. This issue has been addressed in a number of ways over the years. One common approach to reducing post-stimulation polarization is to provide a high-surface area coating having a micron or sub-micron sized topography, such as a porous sintered metallic coating, a metal oxide coating, or a coating of platinum black. However, further development in post-stimulation polarization levels is desirable.

BRIEF SUMMARY OF THE INVENTION

The present invention relates to an implantable medical electrode and a method of fabricating the implantable medical electrode. The implantable medical electrode includes an electrode substrate having an exterior surface, and a zirconium nitride (ZrN) coating disposed over the exterior surface of the electrode substrate. The ZrN coating reduces post-stimulation polarization on the implantable medical electrode, thereby improving stimulation and sensing capabilities.

BRIEF DESCRIPTION OF THE DRAWINGS

FIG. 1 is a top view of an endocardial pacing lead that includes implantable medical electrodes having ZrN coatings.

DETAILED DESCRIPTION

Figure 2A:
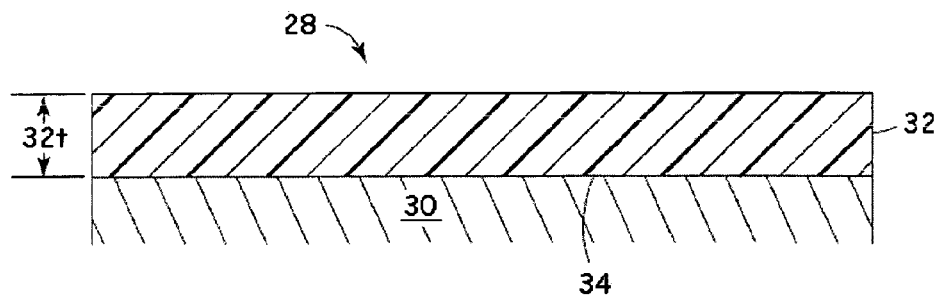
FIG. 2A is a sectional view of an implantable medical electrode having a ZrN coating.

FIG. 1 is a top view of lead 10, which is an endocardial pacing lead that includes proximal end 12 and distal end 14. Proximal end 12 is an in-line bipolar connector assembly for connecting to an implantable medical device (not shown). Distal end 14 includes insulative sheath 16, conductors 18 and 20, anode 22, cathode 24, and tines 26. Insulative sheath 16 is a lead body formed from one or more electrically-insulating materials, such as silicone rubber, polyurethane, and other biocompatible polymers. Conductors 18 and 20 are a pair of mutually-insulated conductive components, shown schematically within insulative sheath 16.

Anode 22 and cathode 24 are implantable medical electrodes formed from conductive materials, and which are respectively connected to conductors 18 and 20. As discussed below, one or both of anode 22 and cathode 24 include a ZrN coating. The ZrN coatings increase the active surface areas of anode 22 and cathode 24, which in turn reduce post-pulse polarization of anode 22 and cathode 24. This improves the impulse transmission and sensing capabilities of lead 10.

Tines 26 are mechanical retention components that stabilize lead 10 against adjacent heart tissue when lead 10 is implanted. In alternative embodiments, lead 10 may include other types of mechanical retention components, such as a helical fixation member. Additionally, while lead 10 is illustrated as an endocardial pacing lead in FIG. 1, implantable medical electrodes of the present invention may also be used to reduce post-stimulation polarization (e.g., post-pulse polarization) with any type of implantable medical device that incorporates electrodes. Examples of suitable devices include leads for pacing, cardioverting, defibrillating, nerve stimulating, sensing, and monitoring functions. The present invention may also be applied to subcutaneous electrodes or "can" or "case" electrodes incorporated in the housing of an implantable medical device.

FIG. 2A is a sectional view of electrode 28, which is representative of anode 22 and cathode 24, and includes electrode substrate 30 and ZrN coating 32. Electrode substrate 30 includes exterior surface 34, which is the surface of electrode substrate 30 that faces outside of lead 10. In this embodiment, ZrN coating 32 is disposed directly on exterior surface 34, and is exposed to the external environment in which lead 10 is located.

Electrode substrate 30 is formed from one or more conductive materials, such as titanium, platinum, platinum iridium, niobium, and combinations thereof. As discussed below, electrode substrate 30 may also be conditioned to roughen exterior surface 34, thereby increasing the surface energy and surface area of exterior surface 34. The increased surface energy correspondingly improves the bond between electrode substrate 30 and ZrN coating 32. The increased surface area of exterior surface 34 assists in reducing post-pulse polarization. Additionally, conditioning is believed to improve impedance measurements as a function of frequency by increasing the flat portion of a frequency sweep by more than a decade in frequency.

ZrN coating 32 is a coating that compositionally includes at least about 95% by weight ZrN, with a particularly suitable composition including at least about 99.9% by weight ZrN. ZrN coating 32 is formed on exterior surface 34 by electrochemical deposition for a duration sufficient to obtain layer thickness $32t$. Examples of suitable electrochemical deposition techniques that may be used to form ZrN coating 32 include sputter deposition, chemical vapor deposition, plasma-enhanced chemical vapor deposition, and cold spray techniques. Examples of suitable thicknesses for layer thickness $32t$ range from about 0.1 micrometers to about 100 micrometers, with particularly suitable thicknesses ranging from about 0.1 micrometers to about 50 micrometers, and with even more particularly suitable thicknesses ranging from about 0.5 micrometers to about 15 micrometers.

ZrN coating 32 further increases the active surface area of electrode 28, thereby reducing the charge intensity that is accumulated on exterior surface 34. As a result, post-pulse polarization is reduced, which correspondingly improves the impulse transmission and sensing capabilities of lead 10. Post-pulse polarization levels obtainable with electrode 28 are similar to those obtained with ruthenium oxide and iridium oxide coatings (e.g., post-pulse polarization levels ranging from about 0.2 millivolts to about 20 millivolts).

Figure 2B:
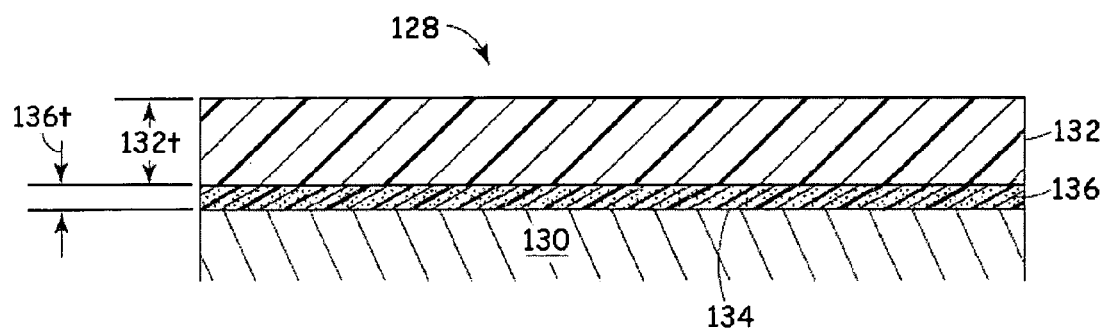
FIG. 2B is a sectional view of an alternative implantable medical electrode having an adhesive coating and a ZrN coating.

FIG. 2B is an expanded sectional view of electrode 128, which is an alternative to electrode 28 shown above in FIG. 2A. Electrode 128 includes electrode substrate 130, ZrN coating 132, and adhesive coating 136, where electrode substrate 130 and ZrN coating 132 are the same as electrode substrate 30 and ZrN coating 32, discussed above. In this embodiment, adhesive coating 136 is disposed between electrode substrate 130 and ZrN coating 132, thereby increasing the bond strength between electrode substrate 130 and ZrN coating 132. As such, ZrN coating 132 is formed on adhesive coating 136, and is not disposed directly on electrode substrate 130. Accordingly, the term "disposed over", with reference to "the ZrN coating being disposed over the exterior surface of the electrode substrate" herein encompasses situations where the ZrN coating is disposed directly on the exterior surface of the electrode substrate (as shown above in FIG. 2A), and situations where one or more intermediate layers are disposed between the ZrN coating and the exterior surface of the electrode substrate (e.g., as shown in FIG. 2B).

Adhesive coating 136 may be formed from a variety of materials to increase the interlayer adhesion between electrode substrate 130 and ZrN coating 132. Examples of suitable materials for adhesive coating 136 include titanium, zirconium, and combinations thereof. Adhesive coating 136 may be formed on exterior surface 134 in variety of manners, including electrochemical deposition techniques. Examples of suitable thicknesses for layer thickness 136$t$ range from about 100 angstroms to about 5,000 angstroms, with particularly suitable thicknesses ranging from about 500 angstroms to about 1,500 angstroms.

Figure 3:
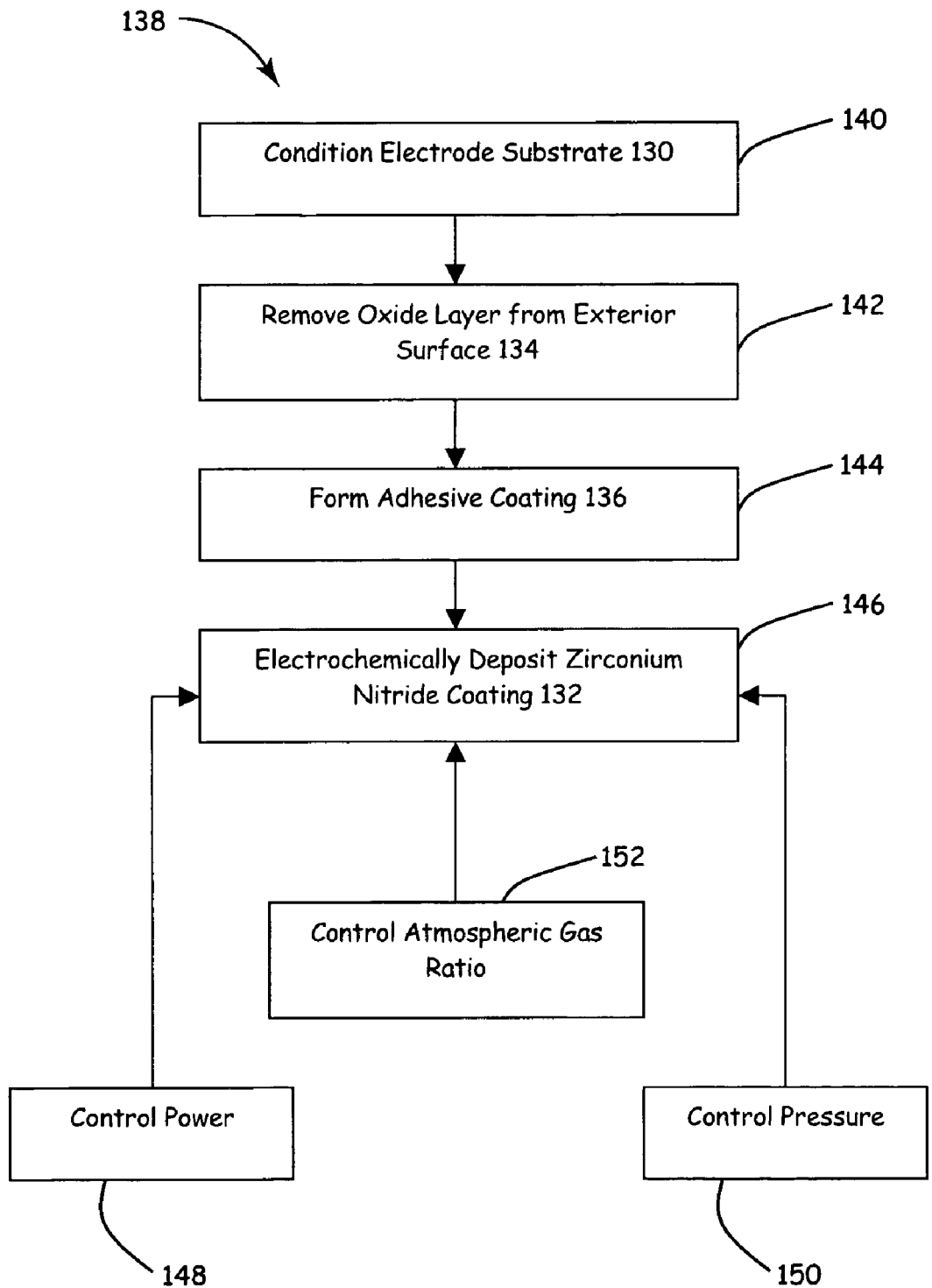
FIG. 3 is a flow diagram illustrating a method of fabricating an implantable medical electrode having a ZrN coating.

FIG. 3 is a flow diagram illustrating method 138 for fabricating electrode 128. While discussed herein with reference to electrode 128, method 138 is suitable for manufacturing a variety of implantable medical electrodes of the present invention (e.g., electrode 28). Method 138 includes step 140-152, and initially involves conditioning electrode substrate 130 (step 140). Electrode substrate 130 may be conditioned using a variety of mechanical or chemical techniques to roughen exterior surface 134. The particular conditioning technique used may vary depending on the conductive materials used for electrode substrate 130.

Examples of suitable conditioning techniques include abrasive blasting and soda blasting exterior surface 134. Abrasive blasting, such as grit blasting with alumina oxide media having average particle sizes of 50-micrometers, roughens exterior surface 134. This correspondingly increases the surface energy and surface area of exterior surface 134. Following the abrasive blasting, electrode substrate 130 may be cleaned and dried. Suitable cleaning techniques include ultrasonic cleaning with solvents (e.g., acetone and isopropanol), and high-pressure washing with water or solvents.

During electrode fabrication, an oxide layer typically forms over the electrode surface (e.g., exterior surface 134) upon exposure to air. The presence of the oxide layer increases the risk of interlayer delamination between electrode substrate 130 and ZrN coating 132 when electrode 128 is exposed to biphasic loads. To reduce the risk of interlayer delamination, the oxide layer is removed from exterior surface 134 prior to depositing ZrN coating 132. A suitable technique for removing the oxide layer includes ion-etching exterior surface 134. After ion-etching, electrode substrate 130 is desirably quarantined from oxygen-containing gases (e.g., air) to prevent a subsequent oxide layer from forming.

After removing the oxide layer, adhesive coating 136 is formed on exterior surface 134 (step 144). As discussed above, adhesive layer 136 may be formed by electrochemically depositing (e.g., sputtering) the adhesive materials onto exterior surface 134. The deposition is desirably performed under vacuum conditions or in an inert gas, oxygen-free atmosphere to prevent oxide layers from being formed. The deposition duration is sufficient to form adhesive coating 136 having a layer thickness 136$t$, which is dependent on the processing parameters. The electrochemical deposition secures adhesive layer 134 to exterior surface 134 of electrode substrate 130.

In alternative embodiments of method 138, one or more of steps 140, 142, and 144 may be omitted. For example, after conditioning (step 140), adhesive coating 136 may be formed on exterior surface 134 (step 144) without removing an formed oxide layer. In this embodiment, adhesive coating 136 may provide a suitable adhesive strength between electrode substrate 130 and ZrN coating 132 to reduce the risk of interlayer delamination.

ZrN coating 132 is then formed on adhesive coating 136 (or directly on exterior surface 134 if step 144 is omitted) by electrochemical deposition (step 146). A particularly suitable electrochemical deposition technique includes sputtering from a zirconium target in the presence of a nitrogen-inert gas (e.g., argon) atmosphere. A suitable system for sputtering includes the trade designated "PerkinElmer 2400" Sputtering System, which is commercially available from PerkinElmer, Inc., Shelton, Conn., and which may be modified to sputter in direct current mode. The sputtering forms zirconium ions and nitrogen ions, which deposit onto adhesive layer 136. This forms ZrN layer 132 on adhesive layer 136, and over exterior surface 134 of electrode substrate 130.

During the deposition process, the sputtering power, the nitrogen/inert gas ratio in the processing atmosphere, and the sputtering pressure are controlled to provide desired properties and layer thicknesses 132$t$ for ZrN layer 132 (steps 148, 150, and 152). For step 148, examples of suitable target power levels for sputtering systems range from about 50 watts to about 500 watts, with particularly suitable target power levels ranging from about 100 watts to about 300 watts. For step 150, examples of suitable sputtering pressures range from about 1 millitorr to about 50 millitorr, with particularly suitable sputtering pressures ranging from about 5 millitorr to about 20 millitorr. Finally, for step 152, suitable nitrogen/inert gas ratios in the processing atmosphere range from about 1:99 (i.e., 1% nitrogen/99% inert gas) to about 50:50, with particularly suitable nitrogen/inert gas ratios ranging from about 10:90 to about 25:75, where all ratios are taken on a volumetric flow rate basis.

The suitable processing conditions of steps 148, 150, and 152 provide electrodes (e.g., electrode 128) having reduced post-pulse polarizations. As discussed above, post-pulse polarization levels that are obtainable with electrodes 28 and 128 are similar to those obtained with ruthenium oxide and iridium oxide coatings. This improves the impulse transmission and sensing capabilities of lead 10.

EXAMPLES

The present invention is more particularly described in the following examples that are intended as illustrations only, since numerous modifications and variations within the scope of the present invention will be apparent to those skilled in the art. Unless otherwise noted, all parts and reagents used in the examples were obtained, or are available, from the standard suppliers, or may be synthesized by conventional techniques.

Coated electrodes of Examples 1-13 were each prepared by electrochemically depositing zirconium ions and nitrogen ions onto a titanium electrode under varying processing conditions to form a zirconium nitride coating over the titanium electrode. The electrochemical deposition involved sputtering from a zirconium target in the presence of a nitrogen-argon gas atmosphere. The sputtering system used was a trade designated "PerkinElmer 2400" Sputtering System, which is commercially available from PerkinElmer, Inc., Shelton, Conn., and which was modified to sputter in direct current mode.

Table 1 provides the varying processing conditions used to form zirconium nitride coatings for the coated electrodes of Examples 1-13, which include the target power, the sputtering pressure, the processing atmosphere concentration (i.e., % nitrogen and % argon) on a volumetric flow rate basis, and the deposition time.

TABLE 1

| Example | Target Power (watts) | Sputtering Pressure (millitorr) | % Nitrogen | % Argon | Deposition Time (minutes) | Layer Thickness (angstroms) |
|---|---|---|---|---|---|---|
| Example 1 | 200 | 12 | 17.5 | 82.5 | 78 | 5,417 |
| Example 2 | 100 | 9 | 10.0 | 90.0 | 153 | 5,100 |
| Example 3 | 200 | 12 | 17.5 | 82.5 | 78 | 6,394 |
| Example 4 | 100 | 15 | 25.0 | 75.0 | 153 | 4,369 |
| Example 5 | 300 | 15 | 25.0 | 75.0 | 68 | 6,895 |
| Example 6 | 100 | 9 | 25.0 | 75.0 | 158 | 4,560 |
| Example 7 | 300 | 9 | 25.0 | 75.0 | 68 | 7,914 |
| Example 8 | 300 | 9 | 10.0 | 90.0 | 68 | 9,034 |
| Example 9 | 200 | 12 | 17.5 | 82.5 | 98 | 7,122 |
| Example 10 | 300 | 15 | 10.0 | 90.0 | 68 | 6,617 |
| Example 11 | 100 | 15 | 10.0 | 90.0 | 312 | 6,178 |
| Example 12 | 300 | 9 | 10.0 | 90.0 | 183 | 21,166 |
| Example 13 | 300 | 9 | 10.0 | 90.0 | 37 | 5,621 |

The data in Table 1 illustrates how the processing conditions affect the layer thicknesses of the zirconium nitride coatings. In general, the layer thicknesses were primarily affected by a combination of the target power levels and deposition time. The processing conditions used to form the coated electrodes of Examples 1-13 are suitable processing conditions for forming zirconium nitride coatings pursuant to the present invention. As discussed above, the resulting zirconium nitride coatings reduce post-stimulation polarization, thereby improving stimulation and sensing capabilities.

Although the present invention has been described with reference to preferred embodiments, workers skilled in the art will recognize that changes may be made in form and detail without departing from the spirit and scope of the invention.

The invention claimed is:

1. An implantable medical electrode comprising: an electrode substrate having an exterior surface; a metal adhesive coating disposed over the exterior surface of the electrode substrate; and a sputter-coated zirconium nitride coating disposed over the adhesive coating, wherein the electrode substrate is a first electrode substrate and the zirconium nitride coating is a first zirconium nitride coating, and wherein the implantable medical electrode further comprises: a second electrode substrate having an exterior surface; and a second zirconium nitride coating disposed over the exterior of the second electrode substrate.

2. The implantable medical electrode of claim 1, wherein the metal adhesive coating is selected from the group consisting of titanium, zirconium, and combinations thereof.

3. The implantable medical electrode of claim 1, wherein the exterior surface of the electrode substrate is roughened to increase surface area of the exterior surface.

4. The implantable medical electrode of claim 1, wherein the zirconium nitride coating has a layer thickness ranging from about 0.1 micrometers to about 50 micrometers.

5. The implantable medical electrode of claim 4, wherein the layer thickness of the zirconium nitride coating ranges from about 0.5 micrometers to about 15 micrometers.

6. The implantable medical electrode of claim 1, wherein the metal adhesive coating has a thickness of about 100 Angstroms to about 5000 Angstroms.

7. An implantable medical electrode comprising:
an electrode substrate having an exterior surface;
a metal adhesive coating disposed over the exterior surface of the electrode substrate; and
a zirconium nitride coating disposed over the adhesive coating by a method comprising sputter depositing zirconium ions and nitrogen ions over the adhesive coating;
wherein the electrode has a post-pulse polarization level ranging from about 0.2 millivolt to about 20 millivolts.

8. The implantable medical electrode of claim 7, wherein the metal adhesive coating has a thickness of about 100 Angstroms to about 5000 Angstroms.

9. An implantable medical electrode comprising:
an electrode substrate having an exterior surface;
an adhesive coating consisting of an elemental metal disposed over the exterior surface of the electrode substrate; and
a sputter-coated zirconium nitride coating disposed over the adhesive coating.

10. An implantable medical electrode comprising:
an electrode substrate having an exterior surface;
an adhesive coating consisting of an elemental metal disposed over the exterior surface of the electrode substrate; and
a zirconium nitride coating disposed over the adhesive coating by a method comprising sputter depositing zirconium ions and nitrogen ions over the adhesive coating;
wherein the electrode has a post-pulse polarization level ranging from about 0.2 millivolt to about 20 millivolts.

11. An implantable medical electrode comprising:
an electrode substrate having an exterior surface;
an adhesive coating disposed over the exterior surface of the electrode substrate, wherein the adhesive coating has a thickness of about 100 Angstroms to 5000 Angstroms; and
a sputter-coated zirconium nitride coating disposed over the adhesive coating.

12. The implantable medical electrode of claim 11, wherein the adhesive coating has a thickness of about 500 Angstroms to about 1500 Angstroms.

13. An implantable medical electrode comprising:
an electrode substrate having an exterior surface;

an adhesive coating disposed over the exterior surface of the electrode substrate, wherein the adhesive coating has a thickness of about 100 Angstroms to 5000 Angstroms; and a zirconium nitride coating disposed over the adhesive coating by a method comprising sputter depositing zirconium ions and nitrogen ions over the adhesive coating; wherein the electrode has a post-pulse polarization level ranging from about 0.2 millivolt to about 20 millivolts.

14. The implantable medical electrode of claim 13, wherein the adhesive coating has a thickness of about 500 Angstroms to about 1500 Angstroms.

* * * * *